US006162168A

United States Patent [19]
Schweich, Jr. et al.

[11] Patent Number: 6,162,168
[45] Date of Patent: *Dec. 19, 2000

[54] HEART WALL TENSION REDUCTION APPARATUS

[75] Inventors: Cyril J. Schweich, Jr., St. Paul; Todd J. Mortier, Minneapolis, both of Minn.

[73] Assignee: Myocor, Inc., St. Paul, Minn.

[*] Notice: This patent is subject to a terminal disclaimer.

[21] Appl. No.: 09/492,777

[22] Filed: Jan. 28, 2000

Related U.S. Application Data

[63] Continuation of application No. 08/778,277, Jan. 2, 1997, Pat. No. 6,050,936.
[51] Int. Cl.[7] .......................... A61M 31/00; A61B 17/12
[52] U.S. Cl. ............................... 600/16; 600/37; 128/898
[58] Field of Search .................. 607/16–18, 37; 601/11; 623/3, 11; 128/897, 898

[56] References Cited

U.S. PATENT DOCUMENTS

| Re. 34,021 | 8/1992 | Mueller et al. ............... 604/51 |
| 4,192,293 | 3/1980 | Asrican ........................ 600/18 |
| 4,261,342 | 4/1981 | Aranguren Duo ............. 128/1 |
| 4,372,293 | 2/1983 | Vijil-Rosales ................. 128/1 |
| 4,409,974 | 10/1983 | Freedland ..................... 128/92 |
| 4,536,893 | 8/1985 | Parravicini ................... 623/3 |
| 4,936,857 | 6/1990 | Kulik ............................ 623/3 |
| 4,944,753 | 7/1990 | Burgess et al. ............... 623/16 |
| 4,960,424 | 10/1990 | Grooters ....................... 623/2 |
| 4,997,431 | 3/1991 | Isner et al. ................... 606/15 |
| 5,106,386 | 4/1992 | Isner et al. ................... 606/15 |
| 5,131,905 | 7/1992 | Grooters ....................... 600/16 |
| 5,169,381 | 12/1992 | Snyders ........................ 600/16 |
| 5,192,314 | 3/1993 | Daskalakis .................... 623/3 |
| 5,250,049 | 10/1993 | Michael ........................ 606/72 |
| 5,284,488 | 2/1994 | Sideris ......................... 606/213 |
| 5,385,528 | 1/1995 | Wilk ............................. 600/18 |
| 5,433,727 | 7/1995 | Sideris ......................... 606/213 |
| 5,450,860 | 9/1995 | O'Connor .................... 128/898 |
| 5,452,733 | 9/1995 | Sterman et al. .............. 128/898 |
| 5,458,574 | 10/1995 | Machold et al. ............. 604/101 |
| 5,496,305 | 3/1996 | Kittrell et al. ................ 606/15 |

(List continued on next page.)

FOREIGN PATENT DOCUMENTS

| 0 583 012 | 2/1994 | European Pat. Off. . |
| 2 768 324 | 3/1999 | France . |
| 296 19 294 U | 8/1987 | Germany . |
| 36 14 292 | 11/1987 | Germany . |
| 42 34 127 | 5/1994 | Germany . |
| 91/19465 | 12/1991 | WIPO . |
| 95/06447 | 3/1995 | WIPO . |
| 95/16476 | 6/1995 | WIPO . |
| 96/04852 | 2/1996 | WIPO . |
| 96/40356 | 12/1996 | WIPO . |
| 97/24101 | 7/1997 | WIPO . |
| 98/03213 | 1/1998 | WIPO . |
| 98/18393 | 5/1998 | WIPO . |
| 98/26738 | 6/1998 | WIPO . |
| 98/29041 | 7/1998 | WIPO . |
| 98/32382 | 7/1998 | WIPO . |
| 99/13777 | 3/1999 | WIPO . |
| 99/44534 | 9/1999 | WIPO . |
| 00/13722 | 3/2000 | WIPO . |
| 00/18320 | 4/2000 | WIPO . |

OTHER PUBLICATIONS

Edie, M.D. et al., "Surgical repair of single ventricle,"*The Journal of Thoracic and Cardiovascular Surgery*, vol. 66, No. 3, Sep., 1973, pp. 350–360.

McGoon, M.D. et al., "Correction of the univentricular heart having two atrioventricular valves," *The Journal of Thoracic and Cardiovascular Surgery*, vol. 74, No. 2, Aug., 1977, pp. 218–226.

Lev, M.D., et al., "Single (Primitive) Ventricle," *Circulation*, vol. 39, May, 1969, pp. 577–591.

(List continued on next page.)

*Primary Examiner*—Jeffrey R. Jastrzab
*Attorney, Agent, or Firm*—Finnegan, Henderson, Farabow, Garrett & Dunner

[57] ABSTRACT

An apparatus for treatment of a failing heart by reducing the wall tension therein. In one embodiment, the apparatus includes a tension member for drawing at least two walls of a heart chamber toward each other.

71 Claims, 3 Drawing Sheets

U.S. PATENT DOCUMENTS

| | | | |
|---|---|---|---|
| 5,509,428 | 4/1996 | Dunlop | 128/898 |
| 5,533,958 | 7/1996 | Wilk | 600/18 |
| 5,571,215 | 11/1996 | Sterman et al. | 623/66 |
| 5,584,803 | 12/1996 | Stevens et al. | 604/4 |
| 5,593,424 | 1/1997 | Northrup, III | 606/232 |
| 5,682,906 | 11/1997 | Sterman et al. | 128/898 |
| 5,702,343 | 12/1997 | Alferness | 607/37 |
| 5,718,725 | 2/1998 | Sterman et al. | 623/2 |
| 5,800,334 | 9/1998 | Wilk | 600/18 |
| 5,800,528 | 9/1998 | Lederman et al. | 623/3 |
| 5,814,097 | 9/1998 | Sterman et al. | 623/2 |
| 5,849,005 | 12/1998 | Garrison et al. | 606/1 |
| 5,855,614 | 1/1999 | Stevens et al. | 623/11 |
| 5,865,791 | 2/1999 | Whayne et al. | 604/49 |
| 5,957,977 | 9/1999 | Melvin | 623/3 |
| 5,984,857 | 11/1999 | Buck et al. | 606/16 |
| 6,024,756 | 2/2000 | Huebsch et al. | 606/213 |

OTHER PUBLICATIONS

Westaby with Bosher, "Landmarks in Cardiac Surgery," 1977, pp. 198–199.

Shumacker, "Cardiac Aneurysms," *The Evolution of Cardiac Surgery*, 1992, pp. 159–165.

Feldt, M.D., "Current status of the septation procedure for univentricular heart," *The Journal of Thoracic and Cardiovascular Surgery*, vol. 82, No. 1, Jul., 1981, pp. 93–97.

Doty, M.D., "Septation of the univentricular heart," *The Journal of Thoracic and Cardiovascular Surgery*, vol. 78, No. 3, Sep., 1979, pp. 423–430.

Carpentier et al., "Myocardial Substitution with a Stimulated Skeletal Muscle: First Successful Clinical Case," Letter to the Editor, p. 1267, Sep. 25, 1996.

Ianuzzo et al., "Preservation of the Latissimus Dorsi Muscle During Cardiomyoplasty Surgery," *J. Card. Surg.*, 1996:11:99–108.

Ianuzzo et al., "On Preconditioning of Skeletal Muscle: Application to Dynamic Cardiomyoplasty," Invited Commentary, *J. Card. Surg.*, 1996:11:109–110.

Chachques et al., "Latissimus Dorsi Dynamic Cardiomyoplasty," *Ann. Thorac. Surg.*, 1989:47:600–604.

Moreira et al., "Latissimus Dorsi Cardiomyoplasty in the Treatment of Patients with Dilated Cardiomyopathy," Supplement IV Circulation, Sep. 25, 1996, 7 pgs.

Lucas et al., "Long–Term Follow–Up (12 to 35 Weeks) After Dynamic Cardiomyoplasty," *JACC*, vol. 22, No. 3, Sep. 1993:758–67.

Batista et al., "Partial Left Ventriculectomy to Improve Left Ventricular Function in End–Stage Heart Disease," *J. Card. Surg.*, 1996:11:96–98.

"Congestive Heart Failure in the United States: A New Epidemic" Data Fact Sheet, National Heart, Lung, and Blood Institute, National Institutes of Health, Dec. 9, 1996, pp. 1–6.

Kormos et al., "Experience with Univentricular Support in Mortally III Cardiac Transplant Candidates," *Ann. Thorac. Surg.*, 1990:49:261–71.

Wampler et al., "Treatment of Cardiogenic Shock with the Hemopump Left Ventricular Assist Device," *Ann. Thorac. Surg.*, 1991:52:506–13.

McCarthy et al., "Clinical Experience with the Novacor Ventricular Assist System," *J. Thorac. Cardiovasc. Surg.*, 1991:102–578–87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626–628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629–631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632–636.

Bearnson et al., "Development of a Prototype Magnetically Suspended Rotor Ventricular Assist Device," *ASAIO Journal*, 1996, pp. 275–280.

Sakakibara et al., "A Muscle Powered Cardiac Assist Device for Right Ventricular Support: Total Assist or Partial Assist?," *Trans. Am.Soc. Artif. Intern. Organs*, vol. XXXVI, 1990, pp. 372–375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release date Sep. 26, 1996, ABIOMED's Temporary Artificial Heart System Reaches 200 U.S. Medical Center Milestone, 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED Wins NIH Grant to Develop Calcification–Resistant Plastic Heart Valve," 1 page.

Press Release dated Aug. 25, 1995; "ABIOMED Wins Research Grant from NIH to Develop Suturing Instrument for Abdominal surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS–5000 in More Than 100 U.S. Medical Centers," 1 page.

"Reversible Cardiomyopathy," *Thoratec's Heartbeat*, vol. 10.2, Aug. 1996, 4 pages.

Tsai et al., "Surface Modifying Additives for Improved Device–Blood Compatibility," *ASAIO Journal*, 1994, pp. 619–624.

Farrar et al., "A New Skeletal Muscle Linear–Pull Energy Convertor as a Power Source for Prosthetic Support Devices," *The Journal of Heart & Lung Transplantation*, vol. 11, No. 5, Sep., 1992, pp. 341–349.

Brochure entitled "Thoratec Ventricular Assist Device System—Because Heart Patients Come in All Sizes," date even with or prior to Jan. 2, 1997, 5 pages.

Press Release dated Oct. 3, 1994, "Heartmate System Becomes First Implantable Cardiac–Assist Device to be Approved for Commercial Sale in the U.S.," 2 pages.

Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

Bach et al., "Early Improvement in Congestive Heart Failure after Correction of Secondary Mitral Regurgitation in End–Stage Cardiomyopathy," *American Heart Journal*, Jun. 1995, pp. 1165–1170.

Schuler et al., "Temporal Response of Left Ventricular Performance to Mitral Valve Surgery," vol. 59, No. 6, Jun. 1979, pp. 1218–1231.

Huikuri, "Effect of Mitral Valve Replacement on Left Ventricular Function in Mitral Regurgitation," *Br. Heart J.*, vol. 49, 1983, pp. 328–333.

Pitarys II et al., "Long–Term Effects of Excision of the Mitral Apparatus on Global and Regional Ventricular Function in Humans," *JACC*, vol. 15, No. 3, Mar. 1, 1990, pp. 557–563.

Bolling et al., "Surgery for Acquired Heart Disease/Early Outcome of Mitral Valve Reconstruction in Patients with End–Stage Cardiomyopathy," *The Journal of Thoracic and Cardiovascular Surgery*, vol. 109, No. 4, Apr. 1995, pp. 676–683.

Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138–1146.

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the 77$^{th}$ Annual Meeting of the American Association of Thoracic Surgeons, May 1997, 33 pages.

Alonso–Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404–406, Oct. 1987.

Savage, M.D., "Repair of left ventricular aneurysm," *The Journal of Thoracic and Cardiovascular Surgery*, vol. 104, No. 3, Sep., 1992, pp. 752–762.

Melvin, "Ventricular Radius Reduction Without Restriction: A Computational Analysis," *ASAIO Journal*, 45:160–165, 1999.

Cox, "Left Ventricular Aneurysms: Pathophysiologic Observations and Standard Resection," *Seminars in Thoracic and Cardiovascular Surgery*, vol. 9, No. 2, Apr., 1997, pp. 113–122.

Boyd et al., "Tricuspid Annuloplasty," *The Journal of Thoracic Cardiovascular Surgery*, vol. 68, No. 3, Sep. 1974, 8 pages.

HEART WALL TENSION REDUCTION APPARATUS

This is a continuation of application Ser. No. 08/778,277, filed Jan. 2, 1997, now U.S. Pat. No. 6,050,936, which is incorporated herein by reference.

FIELD OF THE INVENTION

The present invention pertains to the field of apparatus for treatment of a failing heart. In particular, the apparatus of the present invention is directed toward reducing the wall stress in the failing heart.

BACKGROUND OF THE INVENTION

The syndrome of heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure with a resulting difference in pathophysiology of the failing heart, such as the dilatation of the left ventricular chamber. Etiologies that can lead to this form of failure include idiopathic cardiomyopathy, viral cardiomyopathy, and ischemic cardiomyopathy.

The process of ventricular dilatation is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Prior art treatments for heart failure fall into three generally categories. The first being pharmacological, for example, diuretics. The second being assist systems, for example, pumps. Finally, surgical treatments have been experimented with, which are described in more detail below.

With respect to pharmacological treatments, diuretics have been used to reduce the workload of the heart by reducing blood volume and preload. Clinically, preload is defined in several ways including left ventricular end diastolic pressure (LVEDP), or left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme inhibitors have been used to treat heart failure through the reduction of cardiac workload through the reduction of afterload. Afterload may be defined as the tension or stress required in the wall of the ventricle during ejection. Inotropes like digoxin are cardiac glycosides and function to increase cardiac output by increasing the force and speed of cardiac muscle contraction. These drug therapies offer some beneficial effects but do not stop the progression of the disease.

Assist devices include mechanical pumps and electrical stimulators. Mechanical pumps reduce the load on the heart by performing all or part of the pumping function normally done by the heart. Currently, mechanical pumps are used to sustain the patient while a donor heart for transplantation becomes available for the patient. Electrical stimulation such as bi-ventricular pacing have been investigated for the treatment of patients with dilated cardiomyopathy.

There are at least three surgical procedures for treatment of heart failure: 1) heart transplant; 2) dynamic cardiomyoplasty; and 3) the Batista partial left ventriculectomy. Heart transplantation has serious limitations including restricted availability of organs and adverse effects of immunosuppressive therapies required following heart transplantation. Cardiomyoplasty includes wrapping the heart with skeletal muscle and electrically stimulating the muscle to contract synchronously with the heart in order to help the pumping function of the heart. The Batista partial left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

SUMMARY OF THE INVENTION

The present invention pertains to a non-pharmacological, passive apparatus for the treatment of a failing heart. The device is configured to reduce the tension in the heart wall. It is believed to reverse, stop or slow the disease process of a failing heart as it reduces the energy consumption of the failing heart, decrease in isovolumetric contraction, increases sarcomere shortening during contraction and an increase in isotonic shortening in turn increases stroke volume. The device reduces wall tension during diastole (preload) and systole.

In one embodiment, the apparatus includes a tension member for drawing at least two walls of the heart chamber toward each other to reduce the radius or area of the heart chamber in at least one cross sectional plane. The tension member has anchoring member disposed at opposite ends for engagement with the heart or chamber wall.

In another embodiment, the apparatus includes a compression member for drawing at least two walls of a heart chamber toward each other. In one embodiment, the compression member includes a balloon. In another embodiment of the apparatus, a frame is provided for supporting the compression member.

Yet another embodiment of the invention includes a clamp having two ends biased toward one another for drawing at least two walls of a heart chamber toward each other. The clamp includes at least two ends having atraumatic anchoring member disposed thereon for engagement with the heart or chamber wall.

DETAILED DESCRIPTION OF THE INVENTION

Figure 1:
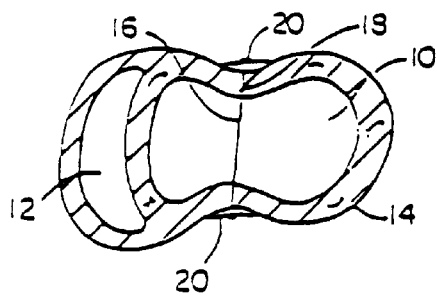
FIG. 1 is a transverse cross-section of the left and right ventricles of a human heart showing the placement of a splint in accordance with the present invention.

Referring now to the drawings wherein like reference numerals refer to like elements throughout the several views, FIG. 1 shows a transverse cross-section of a left ventricle 10 and a right ventricle 12 of a human heart 14. Extending through the left ventricle is a splint 16 including a tension member 18 and oppositely disposed anchors 20. Splint 16 as shown in FIG. 1 has been positioned to draw opposite walls of left ventricle 10 toward each other to reduce the "radius" of the left ventricular cross-section or the cross-sectional area thereof to reduce left ventricular wall stresses. It should be understood that although the splint 16 and the alternative devices disclosed herein are described in relation to the left ventricle of a human heart, these devices could also be used to reduce the radius or cross-sectional area of the other chambers of a human heart in transverse or vertical directions, or at an angle between the transverse and vertical.

Figure 2:
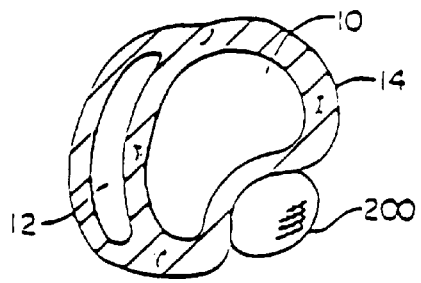
FIG. 2 is a transverse cross-section of the left and right ventricles of a human heart showing the placement of a balloon device in accordance with the present invention.

FIG. 2 discloses an alternate embodiment of the present invention, wherein a balloon 200 is deployed adjacent the left ventricle. The size and degree of inflation of the balloon can be varied to reduce the radius or cross-sectional area of left ventricle 10 of heart 14.

Figure 3:
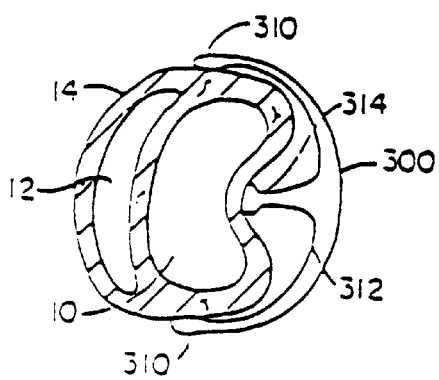
FIG. 3 is a transverse cross-section of the left and right ventricles of a human heart showing the placement of an external compression frame structure in accordance with the present invention.

FIG. 3 shows yet another alternative embodiment of the present invention deployed with respect to left ventricle 10 of human heart 14. Here a compression frame structure 300 is engaged with heart 14 at atraumatic anchor pads 310. A compression member 312 having an atraumatic surface 314 presses against a wall of left ventricle 10 to reduce the radius or cross-sectional area thereof.

Figure 4:
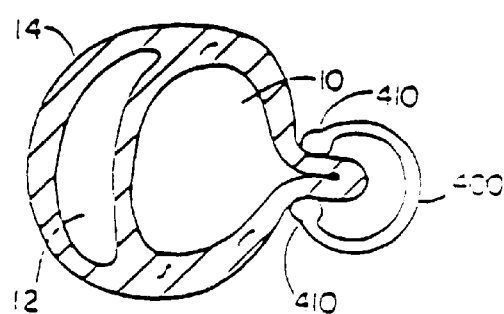
FIG. 4 is a transverse cross-section of the left and right ventricles of a human heart showing a clamp in accordance with the present invention.

FIG. 4 is a transverse cross-sectional view of human heart 14 showing yet another embodiment of the present invention. In this case a clamp 400 having atraumatic anchor pads 410 biased toward each other is shown disposed on a wall of left ventricle 10. Here the radius or cross-sectional area of left ventricle 10 is reduced by clamping off the portion of the wall between pads 410. Pads 410 can be biased toward each other and/or can be held together by a locking device.

Each of the various embodiments of the present invention disclosed in FIGS. 1–4 can be made from materials which can remain implanted in the human body indefinitely. Such biocompatible materials are well-known to those skilled in the art of clinical medical devices.

Figure 5:
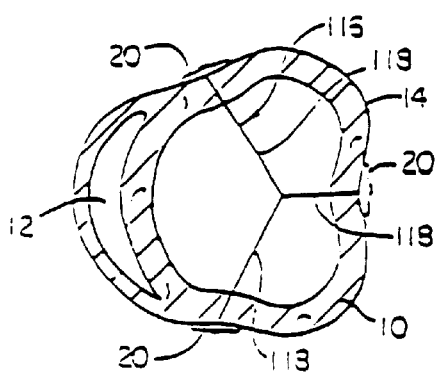
FIG. 5 is a transverse cross-section of the left and right ventricles of a human heart showing a three tension member version of the splint of FIG. 1.
Figure 6:
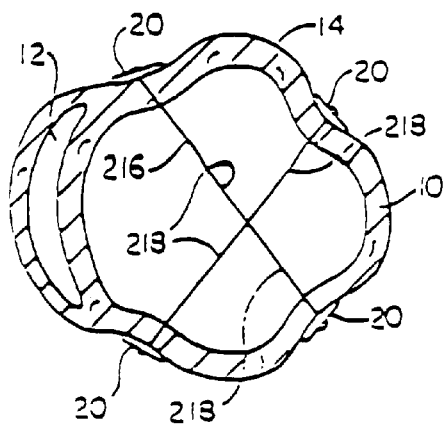
FIG. 6 is a transverse cross-section of the left and right ventricles of a human heart showing a four tension member version of the splint shown in FIG. 1.

FIG. 5 shows an alternate embodiment of the splint of FIG. 1 referred to in FIG. 5 by the numeral 116. The embodiment 116 shown in FIG. 5 includes three tension members 118 as opposed to a single tension member 18 as shown in FIG. 1. FIG. 6 shows yet another embodiment of the splint 216 having four tension members 218. It is anticipated that in some patients, the disease process of the failing heart may be so advanced that three, four or more tension members may be desirable to reduce the heart wall stresses more substantially than possible with a single tension member as shown in FIG. 1.

Figure 7:
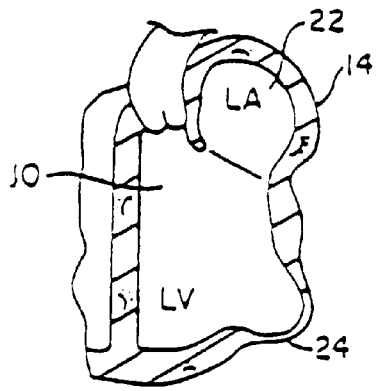
FIG. 7 is a vertical cross-section of the left ventricle and atrium, the left ventricle having scar tissue.

FIG. 7 is a partial vertical cross-section of human heart 14 showing left ventricle 10 and left atrium 22. As shown in FIG. 7, heart 14 includes a region of scar tissue 24 associated with an aneurysm or ischemia. As shown in FIG. 7, the scar tissue 24 increases the radius or cross-sectional area of left ventricle 10 in the region affected by the scar tissue. Such an increase in the radius or cross-sectional area of the left ventricle will result in greater wall stresses on the walls of the left ventricle.

Figure 8:
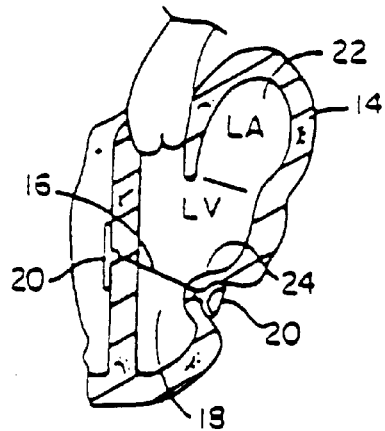
FIG. 8 is a vertical cross-section of the heart of FIG. 7 showing the splint of FIG. 1 drawing the scar tissue toward the opposite wall of the left ventricle.

FIG. 8 is a vertical cross-sectional view of the heart 14 as shown in FIG. 7, wherein a splint 16 has been placed to draw the scar tissue 24 toward an opposite wall of left ventricle 10. As a consequence of placing splint 16, the radius or cross-sectional area of the left ventricle affected by the scar tissue 24 is reduced. The reduction of this radius or cross-sectional area results in reduction in the wall stress in the left ventricular wall and thus improves heart pumping efficiency.

Figure 9:
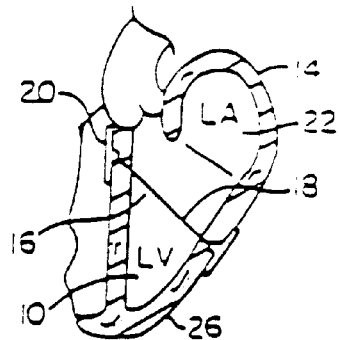
FIG. 9 is a vertical cross-section of the left ventricle and atrium of a human heart showing a version of the splint of FIG. 1 having an elongate anchor bar.

FIG. 9 is a vertical cross-sectional view of left ventricle 10 and left atrium 22 of heart 14 in which a splint 16 has been placed. As shown in FIG. 9, splint 16 includes an alternative anchor 26. The anchor 26 is preferably an elongate member having a length as shown in FIG. 9 substantially greater than its width (not shown). Anchor bar 26 might be used to reduce the radius or cross-sectional area of the left ventricle in an instance where there is generalized enlargement of left ventricle 10 such as in idiopathic dilated cardiomyopathy. In such an instance, bar anchor 26 can distribute forces more widely than anchor 20.

Figure 10:
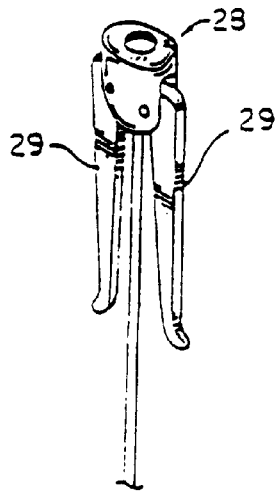
FIG. 10 is a side view of an undeployed hinged anchor member.
Figure 11:
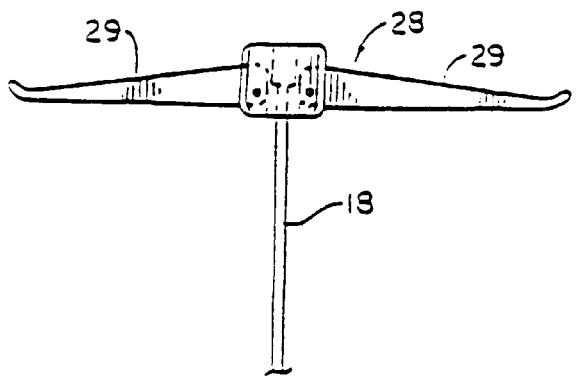
FIG. 11 is a side view of a deployed hinged anchor member of FIG. 10.

FIGS. 10 and 11 are side views of a hinged anchor 28 which could be substituted for anchors 20 in undeployed and deployed positions respectively. Anchor 28 as shown in FIG. 10 includes two legs similar to bar anchor 26. Hinged anchor 28 could include additional legs and the length of those legs could be varied to distribute the force over the surface of the heart wall. In addition there could be webbing between each of the legs to give anchor 28 an umbrella-like appearance. Preferably the webbing would be disposed on the surface of the legs which would be in contact with the heart wall.

Figure 12:
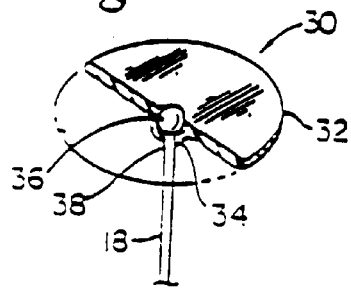
FIG. 12 is a cross-sectional view of an captured ball anchor member.

FIG. 12 is a cross-sectional view of a capture ball anchor 30. Capture ball anchor 30 can be used in place of anchor 20. Capture ball anchor 30 includes a disk portion 32 to distribute the force of the anchor on the heart wall, and a recess 34 for receiving a ball 36 affixed to an end of tension member 18. Disk 32 and recess 34 include a side groove which allows tension member 38 to be passed from an outside edge of disk 32 into recess 34. Ball 36 can then be advanced into recess 34 by drawing tension member 18 through an opening 38 in recess 34 opposite disk 32.

Figure 13:
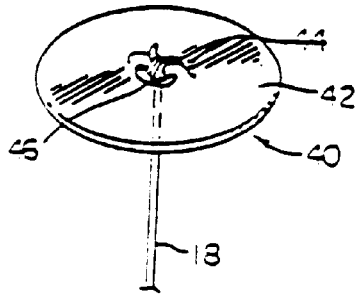
FIG. 13 is a perspective view of a cross bar anchor member.

FIG. 13 is a perspective view of a cross bar anchor 40. The cross bar anchor 40 can be used in place of anchors 20. The anchor 40 preferably includes a disk or pad portion 42 having a cross bar 44 extending over an opening 46 in pad 42. Tension member 18 can be extended through opening 46 and tied to cross bar 42 as shown.

In use, the various embodiments of the present invention are placed in or adjacent the human heart to reduce the radius or cross-section area of at least one chamber of the heart. This is done to reduce wall stress or tension in the heart or chamber wall to slow, stop or reverse failure of the heart. In the case of the splint 16 shown in FIG. 1, a canula can be used to pierce both walls of the heart and one end of the splint can be advanced through the canula from one side of the heart to the opposite side where an anchor can be affixed or deployed. Likewise, an anchor is affixed or deployed at the opposite end of splint 16.

Figure 14:
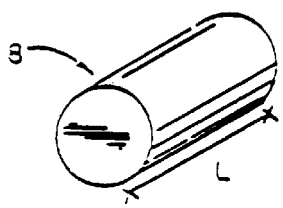
FIG. 14 is a idealized cylindrical model of a left ventricle of a human heart.

FIG. 14 is a view of a cylinder or idealized heart chamber 48 which is used to illustrate the reduction of wall stress in a heart chamber as a result of deployment of the splint in accordance with the present invention. The model used herein and the calculations related to this model are intended merely to illustrate the mechanism by which wall stress is reduced in the heart chamber. No effort is made herein to quantify the actual reduction which would be realized in any particular in vivo application.

Figure 15:
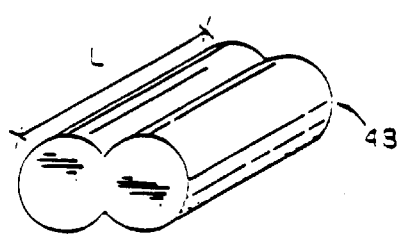
FIG. 15 is a splinted model of the left ventricle of FIG. 14.

FIG. 15 is a view of the idealized heart chamber 48 of FIG. 14 wherein the chamber has been splinted along its length L such that a "figure eight" cross-section has been formed along the length thereof. It should be noted that the perimeter of the circular transverse cross-section of the chamber in FIG. 14 is equal to the perimeter of the figure eight transverse cross-section of FIG. 15. For purposes of this model, opposite lobes of the figure in cross-section are assumed to be mirror images.

Figure 16:
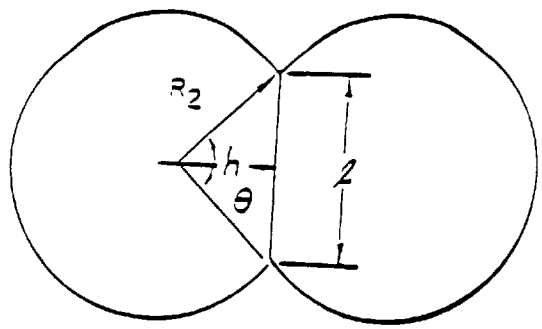
FIG. 16 is a transverse cross-sectional view of FIG. 15 showing various modeling parameters.

FIG. 16 shows various parameters of the FIG. 8 cross-section of the splinted idealized heart chamber of FIG. 15. Where l is the length of the splint between opposite walls of the chamber, $R_2$ is the, radius of each lobe, $\theta$ is the angle between the two radii of one lobe which extends to opposite ends of the portion of the splint within chamber 48 and h is the height of the triangle formed by the two radii and the portion of the splint within the chamber 48 ($R_1$ is the radius of the cylinder of FIG. 14). These various parameters are related as follows:

$$h = R_2 \cos(\theta/2)$$

$$l = 2R_2 \sin(\theta/2)$$

$$R_2 = R_1 \pi / (2\pi - 74)$$

From these relationships, the area of the figure eight cross-section can be calculated by:

$$A_2 = 2\pi(R_2)^2 (1 - \pi/2\pi) + hl$$

Where chamber 48 is unsplinted as shown in FIG. 14 $A_1$, the original cross-sectional area of the cylinder is equal to $A_2$ where $\theta = 180°$, h=0 and $l = 2R_2$. Volume equals $A_2$ times length L and circumferential wall tension equals pressure within the chamber times $R_2$ times the length L of the chamber.

Thus, for example, with an original cylindrical radius of four centimeters and a pressure within the chamber of 140 mm of mercury, the wall tension T in the walls of the cylinder is 104.4 newtons. When a 3.84 cm splint is placed as shown in FIGS. 15 and 16 such that l=3.84 cm, the wall tension T is 77.33 newtons.

Figure 17:
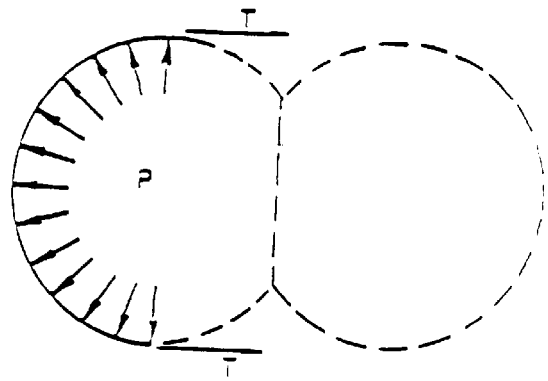
FIG. 17 is a transverse cross-section of the splinted left ventricle of FIG. 15 showing a hypothetical force distribution.
Figure 18:
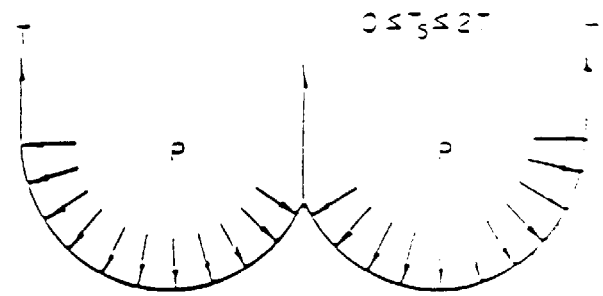
FIG. 18 is a second transverse cross-sectional view of the model left ventricle of FIG. 15 showing a hypothetical force distribution.

FIGS. 17 and 18 show a hypothetical distribution of wall tension T and pressure P for the figure eight cross-section. As $\theta$ goes from 180° to 0°, tension $T_s$ in the splint goes from 0 to a 2T load where the chamber walls carry a T load.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A device for treatment of a heart, the device comprising:
   a static member configured to be positioned adjacent a wall of a heart chamber; and
   an anchoring mechanism coupled to the member to engage the wall of the heart chamber,
   wherein the device is configured to draw portions of the chamber wall toward each other during at least a portion of a cardiac cycle such that all interior parts of the chamber remain in direct fluid communication with each other.

2. The device of claim 1, wherein the member includes first and second opposite ends, and the anchoring mechanism includes an anchoring mechanism provided on each of the first and second opposite ends.

3. The device of claim 1, wherein the member is a tension member configured to be positioned transverse the heart chamber.

4. The device of claim 3, wherein an amount that portions of the chamber wall are drawn toward each other is determined by a length of the tension member transverse the heart chamber.

5. The device of claim 3, wherein the tension member includes more than one tension member configured to be positioned transverse the heart chamber.

6. The device of claim 1, wherein the anchoring mechanism is configured to engage an external surface of the heart wall.

7. The device of claim 1, wherein the member is adapted to remain external the chamber.

8. A device for treatment of a heart, the device comprising:
   a static member configured to be positioned adjacent a wall of a heart chamber; and
   an anchoring mechanism coupled to the member to engage the wall of the heart chamber,
   wherein the device is configured to alter a shape of the chamber during at least a portion of a cardiac cycle such that all interior parts of the chamber remain in direct fluid communication with each other.

9. The device of claim 8, wherein the member includes first and second opposite ends, and the anchoring mechanism includes an anchoring mechanism provided on each of the first and second opposite ends.

10. The device of claim 8, wherein the member is a tension member configured to be positioned transverse the heart chamber.

11. The device of claim 10, wherein an amount that the shape of the chamber is altered is determined by a length of the tension member transverse the heart chamber.

12. The device of claim 10, wherein the tension member includes more than one tension member configured to be positioned transverse the heart chamber.

13. The device of claim 8, wherein the anchoring mechanism is configured to engage an external surface of the heart wall.

14. The device of claim 8, wherein the member is adapted to remain external the chamber.

15. A device for treatment of a heart, the device comprising:
   a static member configured to be positioned adjacent a wall of a heart chamber; and
   an anchoring mechanism coupled to the member to engage the wail of the heart chamber,
   wherein the device is configured to reduce a radius of the chamber during at least a portion of a cardiac cycle such that all interior parts of the chamber remain in direct fluid communication with each other.

16. The device of claim 15, wherein the member includes first and second opposite ends, and the anchoring mechanism includes an anchoring mechanism provided on each of the first and second opposite ends.

17. The device of claim 15, wherein the member is a tension member configured to be positioned transverse the heart chamber.

18. The device of claim 17, wherein an amount that the radius of the chamber is reduced is determined by a length of the tension member transverse the heart chamber.

19. The device of claim 17, wherein the tension member includes more than one tension member configured to be positioned transverse the heart chamber.

20. The device of claim 15, wherein the anchoring mechanism is configured to engage an external surface of the heart wall.

21. The device of claim 15, wherein the member is adapted to remain external the chamber.

22. A device for treatment of a heart, the device comprising:
   a static member configured to be positioned adjacent a wall of a heart chamber; and
   an anchoring mechanism coupled to the member to engage the wall of the heart chamber,
   wherein the device is configured to draw portions of the chamber wall toward each other during at least a portion of a cardiac cycle such that the portions of the chamber wall remain in a non-contacting relationship.

23. The device of claim 22, wherein the member includes first and second opposite ends, and the anchoring mechanism includes an anchoring mechanism provided on each of the first and second opposite ends.

24. The device of claim 22, wherein the member is a tension member configured to be positioned transverse the heart chamber.

25. The device of claim 24, wherein an amount that portions of the chamber wall are drawn toward each other is determined by a length of the tension member transverse the heart chamber.

26. The device of claim 24, wherein the tension member includes more than one tension member configured to be positioned transverse the heart chamber.

27. The device of claim 22, wherein the anchoring mechanism is configured to engage an external surface of the heart wall.

28. The device of claim 22, wherein the member is adapted to remain external the chamber.

29. A device for treatment of a heart, the device comprising:
   a static member configured to be positioned adjacent portions of a wall of a heart chamber; and
   an anchoring mechanism coupled to the member to engage the wall of the heart chamber,
   wherein the device is configured to alter a shape of the chamber during at least portion of a cardiac cycle such that the portions of the wall remain in a non-contacting relationship.

30. The device of claim 29, wherein the member includes first and second opposite ends, and the anchoring mechanism includes an anchoring mechanism provided on each of the first and second opposite ends.

31. The device of claim 29, wherein the member is a tension member configured to be positioned transverse the heart chamber.

32. The device of claim 31, wherein an amount that the shape of the chamber is altered is determined by a length of the tension member transverse the heart chamber.

33. The device of claim 31, wherein the tension member includes more than one tension member configured to be positioned transverse the heart chamber.

34. The device of claim 29, wherein the anchoring mechanism is configured to engage an external surface of the heart wall.

35. The device of claim 29, wherein the member is adapted to remain external the chamber.

36. A device for treatment of a heart, the device comprising:
   a static member configured to be positioned adjacent portions of a wall of a heart chamber; and
   an anchoring mechanism coupled to the member to engage the wall of the heart chamber,
   wherein the device is configured to reduce a radius of the chamber during at least a portion of a cardiac cycle such that the portions of the wall remain in a non-contacting relationship.

37. The device of claim 36, wherein the member includes first and second opposite ends, and the anchoring mechanism includes an anchoring mechanism provided on each of the first and second opposite ends.

38. The device of claim 36, wherein the member is a tension member configured to be positioned transverse the heart chamber.

39. The device of claim 38, wherein an amount that the radius of the chamber is reduced is determined by a length of the tension member transverse the heart chamber.

40. The device of claim 38, wherein the tension member includes more than one tension member configured to be positioned transverse the heart chamber.

41. The device of claim 36, wherein the anchoring mechanism is configured to engage an external surface of the heart wall.

42. The device of claim 36, wherein the member is adapted to remain external the chamber.

43. A device for treating a heart, the device comprising:
an elongate member having first and second oppositely disposed ends;
a first anchoring member attached to the first end of the elongate member; and
a second anchoring member attached to the second end of the elongate member, wherein each of the first and second anchoring members are configured to engage an exterior surface of a wall of the heart to maintain a position of the elongate member transverse the heart chamber.

44. The device of claim 43, wherein each of the first and second anchoring members has a disc-like shape.

45. The device of claim 43, wherein the heart chamber is the left ventricle.

46. The device of claim 43, wherein the first anchoring member is spaced from the second anchoring member.

47. The device of claim 43, wherein the device is configured to draw portions of the heart wall toward each other in a non-contacting relationship when the first and second anchoring members are engaged with the exterior portion of the wall and the elongate member is positioned transverse the heart chamber.

48. The device of claim 43, wherein the first anchoring member is configured to be attached to the elongate member after the elongate member is positioned transverse the heart chamber.

49. The device of claim 43, further comprising a mechanism configured to attach the elongate member to the first and second anchoring members.

50. The device of claim 43, wherein each of the first and second anchoring members define an opening configured to receive the elongate member.

51. A device for treating a heart, the device comprising:
a static member configured to be placed adjacent a wall of an intact heart chamber, the member having a surface adapted to press against the chamber wall to draw portions of the chamber wall towards each other and create a pair of lobes within the chamber that are in direct fluid communication.

52. The device of claim 51, wherein the surface is adapted to press against the chamber wall so that a radius of each of the pair off lobes is less than a radius of the chamber prior to creating the pair of lobes.

53. The device of claim 51, wherein the surface is adapted to press against the chamber wall so that the portions of the chamber wall drawn together remain in a noncontacting relationship.

54. The device of claim 51, wherein the member is adapted to remain external the chamber.

55. The device of claim 51, wherein the member includes at least one anchor device adapted to engage the chamber wall to fix the member in a position adjacent the chamber wall.

56. A system for treating the heart, comprising:
two elongate members each having two oppositely disposed ends; and
four anchoring members, wherein an anchoring member is provided on each of the ends of the elongate members, the anchoring members being configured to engage an exterior wall of a heart chamber to maintain a position of the corresponding elongate member with respect to the heart chamber,
wherein each elongate member and corresponding anchoring members are configured to draw portions of the heart wall toward each other in a non-contacting relationship when the anchoring members are engaged with the exterior wall of the heart chamber and the corresponding elongate member is positioned with respect to the heart chamber.

57. The system of claim 56, wherein the two elongate members are positioned orthogonally relative to each other.

58. A device for treating a heart, the device comprising:
an elongate member having first and second oppositely disposed ends;
a first anchoring member attached to the first end of the elongate member; and
a second anchoring member attached to the second end of the elongate member, wherein the first anchoring member is configured to engage a first exterior surface of a wall of the heart and the second anchoring member is configured to engage a second exterior surface of the wall of the heart to maintain a position of the elongate member transverse a heart chamber, and
wherein during at least a portion of a cardiac cycle, the device is configured to distribute a first force on the first exterior surface that is substantially uniform about the first end of the elongate member, distribute a second force on the second exterior surface that is substantially uniform about the second end of the elongate member, and draw first and second portions of the heart wall toward each other in a non-contacting relationship.

59. The device of claim 58, wherein each of the first and second anchoring members is configured to extend substantially a same distance in both the vertical and transverse directions with respect to the first and second exterior surfaces respectively.

60. A device for treatment of a heart, the device comprising:
a static member configured to surround at least a portion of the heart, the member having a surface adapted to press against a wall of a chamber of the heart to alter a shape of the chamber without a bifurcation of the chamber.

61. The device of claim 60, wherein the member includes first and second opposite ends, and the surface includes a first surface and a second surface provided on the first and second opposite ends respectively.

62. The device of claim 61, wherein the member is adapted to remain external the chamber.

63. The device of claim 61, wherein the member includes first and second anchor pads having the first and second surfaces respectively.

64. A device for treatment of a heart, the device comprising:
a static member configured to be positioned transverse a chamber of the heart, the member having a surface adapted to press against a wall of the chamber to alter a shape of the chamber without a bifurcation of the chamber.

65. The device of claim 64, wherein the member includes first and second opposite ends, and the surface includes a first surface and a second surface provided on the first and second opposite ends respectively.

66. The device of claim 65, wherein the member includes first and second anchor pads having the first and second surfaces respectively.

67. The device of claim 66, wherein the anchor pads are configured to engage an external surface of the heart wall.

68. The device of claim 64, wherein the member includes more than one tension member configured to be positioned transverse the heart chamber.

69. A method for reducing tension within a wall of a heart chamber, comprising the steps of:

surrounding a portion of the chamber with a static member, and forming two directly communicating lobes of the chamber by pressing against the wall of the chamber with a surface of the member.

70. The method of claim 69, further comprising fixing the member in a position so that the surface of the member presses against the wall of the chamber.

71. The method of claim 69, wherein the member includes an anchor pad defining the surface of the member.

* * * * *

UNITED STATES PATENT AND TRADEMARK OFFICE
CERTIFICATE OF CORRECTION

PATENT NO. : 6,162,168
DATED : December 19, 2000
INVENTOR(S) : Cyril J. SCHWEICH, Jr., Todd J. MORTIER It is certified that error appears in the above-identified patent and that said Letters Patent is hereby corrected as shown below:

Claim 15, column 7, line 37, "engage the wail" should read --engage the wall--;

Claim 29, column 8, line 29, --a-- should be inserted after "at least"; and

Claim 52, column 9, line 55; "pair off lobes" should read --pair of lobes--.

Signed and Sealed this

Twenty-fourth Day of April, 2001

Attest:

NICHOLAS P. GODICI

Attesting Officer

Acting Director of the United States Patent and Trademark Office